United States Patent [19]

Davis et al.

[11] 4,119,552

[45] Oct. 10, 1978

[54] LUBRICANT ADDITIVE

[75] Inventors: Bryan Terence Davis; Monty Frederick Crook, both of Wokingham, England

[73] Assignee: Edwin Cooper and Company Limited, Bracknell, England

[21] Appl. No.: 770,579

[22] Filed: Feb. 22, 1977

[30] Foreign Application Priority Data

Feb. 25, 1976 [GB] United Kingdom ............... 7478/76

[51] Int. Cl.² ............................................. C10M 1/54
[52] U.S. Cl. ............................ 252/49.6; 260/559 R; 260/559 T; 260/559 B
[58] Field of Search ................... 252/49.6; 260/559 R, 260/559 T, 559 B

[56] References Cited

U.S. PATENT DOCUMENTS

| | | | |
|---|---|---|---|
| 3,445,498 | 5/1969 | Cyba | 252/49.6 X |
| 3,756,953 | 9/1973 | Piasek et al. | 252/49.6 |
| 4,016,092 | 4/1977 | Andress | 252/49.6 X |

*Primary Examiner*—Paul F. Shaver
*Attorney, Agent, or Firm*—Donald L. Johnson; Robert A. Linn; Joseph D. Odenweller

[57] ABSTRACT

The reaction of a boron compound (e.g., boric acid) with an alkylphenoxy alkanoic acid amide (polyisobutylphenoxyacetamide of tetraethylenepentamine) forms a boronated product useful as a lubricating oil dispersant having improved properties.

22 Claims, No Drawings

LUBRICANT ADDITIVE

BACKGROUND

Alkylphenoxy alkanoic acid amides are known lubricating oil additives. They are described in Otto, U.S. Pat. No. 3,360,464. Boronated alkenylsuccinimide dispersants have likewise been reported in LeSuer, U.S. Pat. No. 3,087,936. Piasek et al, U.S. Pat. No. 3,697,574 describes boronated Mannich condensation products useful as lubricating oil additives.

SUMMARY OF THE INVENTION

This invention relates to lubricant additives, more particularly to novel derivatives of amides of alkaryloxy-substituted alkanoic acids suitable for use as dispersants for lubricating oil.

According to the present invention there is provided a boronated amide of an alkaryloxy-substituted alkanoic acid suitable for use as a lubricating oil additive made by the process comprising reacting an amide of an alkylaryloxy-substituted alkanoic acid wherein said alkyl group contains at least about 30 carbon atoms with a boronating agent, e.g. a boron compound selected from the group consisting of boron acids, esters of boron acids, salts of boron acids with weak bases, boron oxides, boron halides, and boron salts of oxy acids, preferably at a temperature of about 50°–300° C., the amount of said boronating agent being such that said boronated amide has a boron:nitrogen atom ratio of at least about 0.01:1.

The invention also provides a process for making a boronated amide of an alkaryloxy-substituted alkanoic acid, which process comprises reacting a boronating agent, e.g. a boron compound selected from the group consisting of boron acids, esters of boron acids, salts of boron acids with weak bases, boron oxides, boron halides and boron salts of oxy acids, with an amide of an alkaryloxy-substituted alkanoic acid wherein said alkyl group contains at least about 30 carbon atoms, preferably at a temperature of about 50°–300° C., said boronating agent being used in an amount sufficient to provide at least 0.01 atoms of boron per nitrogen atom in the boronated amide.

In another aspect of the present invention there are provided lubricating compositions comprising a major amount of a lubricating oil and a minor amount, e.g. 0.1 to 10% by weight, of a boronated amide in accordance with the present invention.

Also included within the scope of the present invention are additive concentrates comprising a minor amount of a lubricating oil and a major amount of one or more additives in accordance with the present invention, and additive packages comprising a minor amount of a lubricating oil and a major amount of a combination of one or more additives in accordance with the present invention and at least one other lubricant additive.

Amides of alkylaryloxy-substituted alkanoic acids which may be employed as intermediates to the present boronated compounds are described for example in our U.K. Patent Application No. 35732/73. The amides of Application No. 35732/73 may be prepared by amidating an initial compound which is a condensation product of an alkyl-substituted phenol, preferably a p-alkyl-substituted phenol, in which the alkyl substituent contains at least about 30 carbon atoms, preferably about 50–200 carbon atoms, and at least one halogen substituted, preferably α-halogen substituted, aliphatic carboxylic acid or ester thereof. The carboxylic acid may be substituted by two or more halogen atoms, but preferably has a single halogen atom substituent. For the purpose of the condensation reaction by which the initial compounds may be prepared, bromine is more suitable than chlorine as the halogen substituent as the former is more reactive. However, on economic grounds we prefer to use a chloro-substituted carboxylic acid or ester thereof. The initial compounds are more fully described in our U.K. Patent Application No. 9542/73.

Accordingly, the initial compound which is to be amidated may have the general formula:

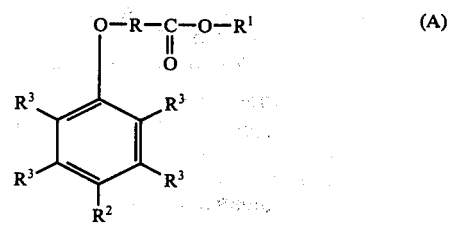

wherein:
(a) each $R^3$ is the same or different and is a hydrogen atom; an alkyl group containing from 1 to 16, preferably 1 to 4, carbon atoms; a halogen atom, preferably a chlorine atom, or one group $R^3$ in the ortho position relative to the oxygen atom attached to the aromatic nucleus is a group of the formula:

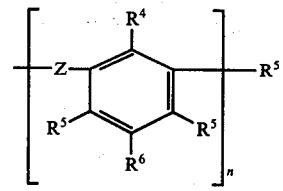

in which
(i) $n$ is an integer of from 1 to 6;
(ii) each Z is the same or different and is a sulphur chain of formula $-S)_m$ wherein $m$ is from 1 to 4, preferably 1 or 2; or a methylene group;
(iii) each $R^4$ is the same or different and is a hydrogen atom; an alkyl group containing from 1 to 16, preferably 1 to 4, carbon atoms; a halogen atom, preferably a chlorine atom; a hydroxyl group; or a group of formula

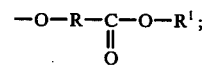

(iv) each $R^5$ is the same or different and is a hydrogen atom; an alkyl group containing from 1 to 16, preferably 1 to 4, carbon atoms; a halogen atom, preferably a chlorine atom; or a hydroxyl group provided that one of, but not more than one of, groups $R^4$ and $R^5$ is a hydroxyl group; and
(v) each $R^6$ is the same or different and is a hydrogen atom; an alkyl group containing from 1 to 29, preferably 1 to 4, carbon atoms; a halogen atom, preferably a chlorine atom; or is as $R^2$;
(vi) provided that one group $R^3$ in the ortho position relative to the oxygen atom attached to the aromatic nucleus is a hydrogen or halogen atom or a methyl or ethyl group;

(b) each R is the same or different and is a straight or branched chain alkylene group containing from 1 to 20, preferably 1 to 12, more preferably 1 to 4, carbon atoms and most preferably is methylene;

(c) each $R^1$ is the same or different and is a hydrogen atom or the residue of a hydroxy compound, preferably the residue of an alkanol containing from 1 to 5 carbon atoms; and (d) each $R^2$ is the same or different and is an alkyl group containing at least about 30 carbon atoms, preferably 50–200 carbon atoms.

In the case of the above defined condensation products the alkyl-substituted phenol starting material may bear one or more additional substituents on the aromatic ring and these correspond to the groups $R^3$ in the initial compounds of the foregoing general formula (A). When no substituent, other than the alkyl substituent corresponding to $R^2$, is present this corresponds to all groups $R^3$ being hydrogen atoms and such compounds are highly preferred. Although $R^2$ in formula (A) is shown in the para position minor amounts of $R^2$ may occur in the ortho position.

The above initial compound to be amidated, as indicated above, can be prepared by a process wherein at least one alkyl-substituted phenol, in which the alkyl substituent contains at least about 30 carbon atoms, is condensed with at least one halogen substituted aliphatic carboxylic acid or ester thereof. In its preferred aspect the process comprises the condensation of at least one p-alkyl substituted phenol of the formula:

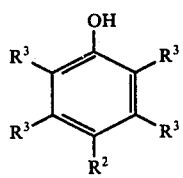

with at least one halogen-substituted aliphatic carboxylic acid or ester thereof of the formula:

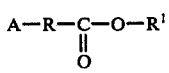

to form a compound of the formula:

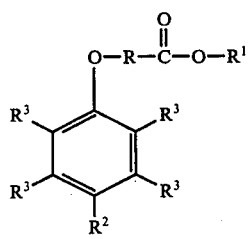
(A)

wherein R, $R^1$, $R^2$ and $R^3$ have the same significance as hereinbefore defined and A is a chlorine or bromine atom. The halogen-substituted carboxylic acid or ester thereof is preferably an α-chloro or α-bromo carboxylic acid or ester thereof and in this case R can be a methylene group (derived from an α-halo-acetic acid or ester thereof) or can be the group

wherein each B is a hydrogen atom or a pendant alkyl group

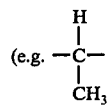

when derived from an α-halo propionic acid or ester thereof).

Thus the groups R and $R^1$ in the product of the process can be determined by the selection of the appropriate halo-substituted carboxylic acid or ester thereof as starting material. Thus $R^1$ is a hydrogen atom when derived from a halo-substituted carboxylic acid. When derived from an ester of a halo-substituted carboxylic acid the esterifying group constituting $R^1$, i.e. the residue of a hydroxy compound, can be any of the well known esterifying groups such as an alkyl group derived from an alkanol; or a glycol monoether or polyoxyalkylene glycol monoether residue.

Alternatively, the hydroxy compound of which $R^1$ is a residue can be a di- or poly-hydroxy compound and the residue will have unused hydroxyl groups; or the hydroxy compound can be a di- or poly-hydroxy compound in which one or more, but not all, the hydroxyl groups have been replaced by groups of the formula:

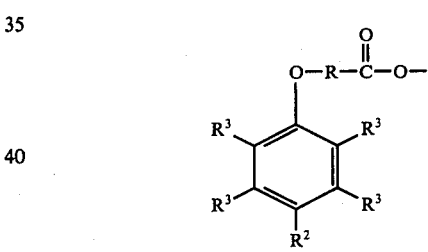

additional to that shown in the foregoing formula (A).

As previously stated, $R^2$ contains at least 30 carbon atoms, preferably 50–200 carbon atoms. In view of this it is highly preferred that $R^1$ in the formula:

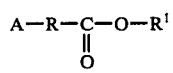

is the residue of a mono- or poly-hydric alkanol. Thus, the reactant which is condensed with the alkyl-substituted phenol is preferably an ester of a halogen-substituted aliphatic carboxylic acid. For example, $R^1$ can be methyl, ethyl, n-propyl, iso-propyl, n-butyl, isobutyl, sec-butyl, n-amyl, iso-amyl, sec-amyl, 2-ethylhexyl, and the like, or can be derived from polyhydric alkanols such as ethylene glycol, propyleneglycol, trimethylolpropane, pentaerythritol, and the like.

The high preference for halogen-substituted aliphatic carboxylic acid esters is because in the case of $C_{30+}$ alkylphenols the degree of reaction is significantly higher when using the ester of the halogen-substituted aliphatic carboxylic acid as compared with using the acid itself. This difference in conversion becomes very significant in determining the nature of the product. In the case of C$_{30+}$ alkylphenols, and especially C$_{50+}$ alkylphenols, it is impractical to separate the unreacted high molecular weight alkylphenol from the reaction mixture. Hence, in the case of the high molecular weight alkyl-phenols the unreacted alkylphenol is retained as a component in the resultant product. This represents an economic loss since it is not an effective dispersant and, furthermore, may represent a performance detriment due to formation of a more corrosive product.

The precise nature of the groups R$^2$ and R$^3$ may be determined by the selection of the appropriate alkyl substituted phenol starting material; and in addition in one particular case described hereinafter by the reaction conditions. Thus, when each R$^3$ is a hydrogen or halogen atom or an alkyl group this is provided by selecting the appropriately substituted phenol starting material. Similarly, compounds in which R$^3$ is a group of formula:

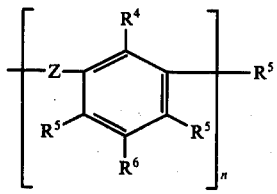

can be prepared from phenol sulphides or derivatives thereof having the appropriate substituents to provide the requisite groups R$^4$, R$^5$ and R$^6$. In this case Z will be a sulphur chain. Compounds in which Z is a methylene group likewise can be prepared from the appropriate o-methylene phenyl derivatives. A particularly useful source of o-methylene phenyl derivatives are phenol/-formaldehyde condensation products.

In all the foregoing variations the alkylphenol starting materials bear the appropriate substituents which, with one exception, constitute the groups R$^4$, R$^5$ and R$^6$. The exception arises when R$^4$ is a hydroxyl group. In this case the starting material will contain two or more phenolic hydroxyl groups and the halo-substituted carboxylic acid may be employed in an amount sufficient to react with a single phenolic hydroxyl group or with all such groups.

Representative examples of alkylphenol starting materials are:
p-triacontylphenol
p-hentriacontyl phenol
p-tetracontyl phenol
p-pentacontyl phenol
polyisobutyl (m.w. 600) phenol
polypropyl (m.w. 850) phenol
polyisobutyl (m.w. 1000) phenol
polyisobutyl (m.w. 1500) phenol
polyisobutyl (m.w. 2000) phenol
polyisobutyl (m.w. 3000) phenol
isobutylene-isoprene butyl rubber (m.w. 30,000) substituted phenol
p-polyisobutyl (m.w. 1000) o-cresol
p-polypropyl (m.w. 1200) o-sec-butylphenol
p-ethylene-propylene copolymer (m.w. 800) o-tert-hexadecyl phenol
4-heptriacontyl-2-chlorophenol
2,2'-methylenebis[4-polyisobutyl (m.w. 1000) phenol]
2,2-isopropylidenebis[polyisobutyl (m.w. 2000) phenol]
2,2-thiobis[polypropyl (m.w. 1200) phenol ]
2,2-tri-thiobis[polyisobutyl (m.w. 800) phenol]
bis(2-hydroxy-polyisobutylphenyl) acetic acid
n-butyl 2,2-bis[2-hydroxypolyisobutyl (m.w. 1200) phenyl]propanoate
hexyl 3,3-bis[2-hydroxypolyisopropyl (m.w. 1100) phenyl]butanoate Representative examples of halo-substituted aliphatic carboxylic acids are as follows:
α-bromo acetic acid
α-chloro acetic acid
α-chloropropionic acid
α-bromo isobutyric acid
3-bromo propionic acid
4-bromo butyric acid
α-chloro eicosanoic acid
α-chloro dodecanoic acid and the like.

Representative examples of the much preferred halo-substituted aliphatic carboxylic acid esters are as follows:
methyl α-bromo acetate
ethyl α-chloro acetate
n-butyl α-chloro acetate
amyl α-chloro acetate
isobutyl α-chloro propanoate
isopropyl α-chloro isobutanoate
2-ethylhexyl 3-bromo propanoate
hexyl 4-bromo butanoate
methyl α-bromo eicosanoate and the like.

It is highly desirable to employ an acid acceptor to neutralise the hydrogen halide liberated in the condensation of the alkylphenol with the halo-substituted carboxylic acid or ester. Such acid acceptors are well known and any suitable material can be used for this purpose, e.g. a tertiary base such as a pyridine. However, the preferred acid acceptor is a metal base such as an alcoholic solution of an alkali metal hydroxide, particularly sodium or potassium hydroxide or an alkali metal or alkaline earth metal alkoxide. The latter can be readily prepared by dissolving the metal in an alcohol, such as methanol or ethanol, in well known manner. The acid acceptor is preferably used in the stoichiometric quantity required to neutralise the hydrogen halide. When using a halo-substituted carboxylic acid, as opposed to the ester thereof, the base will preferentially neutralise the carboxyl group of the acid and additional quantities of base will be required to first neutralise the acid. In this event all the base required to neutralise both carboxylic acid and the hydrogen halide can be added initially to the reaction mixture. Alternatively, sufficient base to neutralise the carboxylic acid may be added initially and the remainder added dropwise during the course of the reaction at a rate sufficient to maintain the reaction mixture just alkaline. Similarly, when using an ester of the halo-substituted carboxylic acid all the base required to neutralise the hydrogen halide may be added initially or the base may be added in portions throughout the reaction. The portion-wise addition of the acid acceptor is the preferred technique.

The condensation reaction proceeds very readily in the presence of the acid acceptor and may be carried out at ambient temperature. Conversely, comparatively high reaction temperatures can also be used up to the decomposition temperature of the reaction mixture. However, to provide a more easily controllable reaction at a rate more rapid than at ambient temperature, a compromise reaction temperature of from 60° C. to 200° C. is preferable, a temperature of from 70° C. to 100° C. being the optimum reaction temperature. Under these conditions the reaction is usually complete within one hour, completion being denoted when no further base is consumed. Dropwise addition of the acid acceptor facilitates the indication of the completion of the reaction in this way. Alternatively, a pH indicator or a pH meter may be used.

The amount of halogen-substituted aliphatic carboxylic acid or ester can vary over a wide range. The ratio is best expressed in terms of moles of reactive halogen-substituted aliphatic carboxylic acid or ester per equivalent of phenolic hydroxyl group. A ratio of 0.7–5 to 1.0 is a useful range. Generally, at least a stoichiometric quantity of halogen-substituted acid or ester is used. A preferred range is about 1.0–1.3 moles of halogen-substituted aliphatic carboxylic acid or ester per equivalent of phenolic hydroxyl.

If desired, the condensation reaction may be carried out in an inert solvent reaction medium, such as a hydrocarbon solvent or alkanol solvent. Examples of such inert solvents are benzene, toluene, xylene, n-butanol, 2-ethylhexanol and mineral oil, especially a mineral oil of lubricating viscosity.

After completion of the reaction the product may, if desired, be washed with water to remove the halide salt of the acid acceptor formed during the reaction. Alternatively the reaction produce may be acidified and washed with aqueous alcohol e.g. aqueous methanol.

The above initial compound is amidated to form the intermediate amide by reaction with an amine containing a reactive hydrogen atom bonded to nitrogen. The resulting amide can be represented by the general formula:

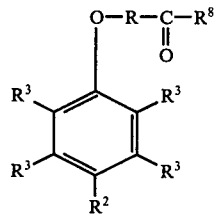

wherein:
(a) R, $R^2$ and $R^3$ are as hereinbefore defined for formula (A)
(b) $R^8$ is the residue of an amine and
(c) with the further provision that $R^4$ as included in the definition of $R^3$ may also be a group of formula

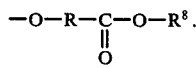

In a preferred embodiment, $R^2$ is an alkyl group, particularly a branched chain alkyl group, containing from 50 to 200 carbon atoms. Such alkyl groups may be derived from long chain olefins such as poly-(alphaolefins), which may have molecular weights in the range of 700 to 3,000, more preferably 900 to 1500 and particularly about 1000. Examples of suitable poly-(alphaolefins) are polyisobutylenes (PIB) and polypropylenes, such as those commercially available under the trade names Hyvis and Indopol. The preferred groups $R^8$ are residues of aliphatic di- or polyamines, the preferred group R is a methylene group and the preferred groups $R^3$ are hydrogen atoms.

The intermediate amides may be prepared from the previously described initial cmpound to be amidated by reaction with an amine which may be selected from a very wide range of amines. The amine employed determines the nature of $R^8$. Useful amines include those having the formula:

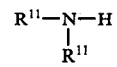

in which each $R^{11}$ is the same or different and is a hydrogen atom or a hydrocarbon, amino-substituted hydrocarbon, hydroxy-substituted hydrocarbon, alkoxy-substituted hydrocarbon, amino, carbamyl, thiocarbamyl or guanyl radical. Preferred amines are di-or polyamino compounds, i.e. wherein at least one group $R^{11}$ is amino-substituted hydrocarbon, and particularly preferred amines are alkylene polyamines having the general formula:

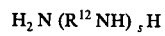

wherein $s$ is an integer and $R^{12}$ is a divalent alkylene radical. Preferably $R^{12}$ is an ethylene radical and $s$ is from 1 to 6, more preferably from 3 to 5. This class of amines is also referred to as "polyalkylenepolyamines" when $s$ is 2 or more. These amines can be prepared by reacting an alkylene dihalide, e.g., 1,2-dichloroethane, with ammonia and they contain in addition to the linear alkylenepolyamines a substantial amount of cyclic alkyleneopolyamines and some branched-chain alkylenepolyamines. All of these components are to be included in the term "alkylenepolyamine" or "polyalkylenepolyamine". Examples of such amines are ethylene diamine, diethylene triamine, triethylene tetramine, tetraethylene pentamine, pentaethylene hexamine and mixed higher polyethylene polyamines. Other alkylene polyamines such as di(1,2-propylene) triamine, or N-(2 amino ethyl)trimethylene diamine may be employed, if desired. Such alkylene polyamines may be first reacted with a α-lactone, preferably α-butyro lactone as described in British Patent Specification No. 1,054,370 or with dicyandiamide as described in British Patent Specification No. 1,068,235.

Other useful alkylene polyamines are the higher polyamines having molecular weights from 300 to 1,000 or 5,000, preferably 400 to 600, especially those prepared by polymerising ethylene imine. The process of polymerising ethylene imine gives rise to mixtures of polyethylene polyamines having a wide range of molecular weights. These may be divided into mixtures having narrow ranges of molecular weights, those indicated being the most useful in this invention.

Other polyamines which may be used are commercially available mixtures such as that predominantly consisting of a mixture of isomeric pentaethylene hexamines of formula $C_{10}H_{28}N_6$ and related hexamines containing piperazine rings and 12 C atoms. The average molecular weight of the mixture is approximately that of pentaethylene hexamine, i.e. 233, and the mixture contains a predominance of amines having 2–4 primary amino groups and at least two secondary amino groups.

Other suitable diamino compounds which may be employed are N-dialkylamino alkylamines of the general formula:

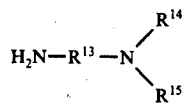

wherein $R^{13}$ is a divalent alkylene radical and $R^{14}$ and $R^{15}$ are alkyl radicals. Examples of such N-dialkylamino alkylamines include dimethylaminomethylamine, dimethylaminoethylamine, dimethylaminopropylamine, dimethylaminobutylamine, dimethylaminoheptylamine, diethylaminomethylamine, diethylaminopropylamine, diethylaminoamylamine, dipropylaminopropylamine, methylpropylaminoamylamine and propylbutylaminoethylamine.

Further suitable diamino compounds are bis (N-aminoalkyl) and N-(β-amino-alkyl) piperazines of formula:

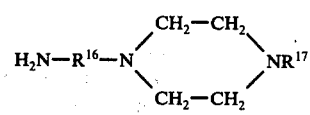

wherein $R^{16}$ is any alkylene radical containing 1 to 3 carbon atoms and $R^{17}$ is a hydrogen atom or a hydrocarbon or aminoalkyl radical containing from 1 to 3 carbon atoms.

Other miscellaneous di- or polyamine compounds which may be used are N-(2-aminoethyl)ethanolamine and hydroxyethyl triethylene tetramine.

The amine may be reacted with the previously described initial compound to be amidated in a wide reactant ratio. A useful range is from about 0.5–10 equivalents of amine per mole of initial compound. An equivalent of amine is a mole divided by the numbers of HN< groups in the molecule. It is preferred that the initial compound be reacted with the amine in approximately equimolar proportions. In this embodiment, when using the preferred alkylene polyamine co-reactants or other amines initially containing two or more primary amino groups, the resulting reaction product will contain one or more residual primary amino groups. Alternatively, with the preferred linear alkylene polyamines the amine may be reacted with up to twice the molar quantity of initial compound or even more. It is not necessary to use exactly molar quantities of the two reactants. Useful additives can be obtained by employing, for example, two moles of the initial compound and 1.5 moles of the alkylene polyamine, giving a mixture of products.

Alternatively, the starting materials are reacted in equimolar proportions and one or more residual amino groups are reacted with a carboxylic acid, to form an amine salt, amide thereof or imidazoline or condensed with aldehydes, ketones or mixtures thereof or with mixtures of aldehydes and phenols to form Mannich bases, in manner known per se. Alternatively, the amine may be first reacted with appropriate quantities of the carboxylic acids, aldehydes, ketones or mixtures of aldehydes and phenols to provide an amine having a residual primary or secondary amino group, and the resulting amine reacted with the initial compounds. In another embodiment, the amine is an alkylene polyamine in which one primary amino group is reacted, either before or after the amine has been reacted in equimolar proportions with the initial compounds, with an alkenyl substituted succinic acid or anhydride thereof containing from 8 to 200 carbon atoms in the alkenyl substituent. Such substituents are preferably derived from comparatively low molecular weight polymers or oligomers of olefins, such as isobutylene or propylene. In view of the foregoing it will be understood that the proportions of the co-reactants may be varied according to the final product required.

The foregoing amidation of the initial compounds may be readily carried out by heating the co-reactants together and a preferred reaction temperature is from 50 to 250° C., more preferably 130° to 220° C., most preferably from 180° to 220° C. An inert solvent, such as xylene, toluene or mineral oil may be used.

The reaction may be most conveniently carried out in a vessel which is open to the atmosphere. However, if desired the reaction can be carried out under vacuum or low pressure conditions or under a nitrogen blanket. The reaction is usually completed within 1 to 6 hours, 2 to 4 hours being most common.

As hereinbefore indicated the preferred amine starting materials are di- or poly-amino compounds, from which amides suitable for boronation according to the present invention can be prepared, which contain two or more nitrogen atoms. Such boronated products are preferred as lubricant additives However, the present invention also includes boronated products derived from ammonia or monoamines, particularly primary or secondary monoamines. Such products may be prepared by reaction of an alkyl-substituted phenol with the appropriate amide of a halogen-substituted carboxylic acid. That is to say the reaction may be carried out in identical manner to the condensation of an alkylphenol with a halogen substituted aliphatic carboxylic acid or ester except that an amide of a halogen-substituted carboxylic acid is used in place of the acid per se or ester thereof. Preferred amides in this case are those derived from ammonia or monoamines containing 1 to 8, more preferably 1 to 4, carbon atoms. The resulting monoamides have utility as intermediates in the preparation of the boronated lubricant additives of the present invention. Alternatively the monoamides may be reacted with the preferred di- or poly-amines in a "transamidation" reaction analogous to a transesterification reaction. This may be carried out by heating the amides derived from ammonia or monoamines with the preferred di- or poly-amines, for example at a temperature of 100° C. to 250° C., more preferably 180° C. to 220° C., while stripping out the more volatile monoamine or ammonia.

In yet another alternative process the amide intermediate may be prepared by reacting the alkyl phenol with an amide derived from a di- or poly-amine and a halogen-substituted aliphatic carboxylic acid in place of the acid per se or ester thereof.

The amide intermediate is boronated to form an additive of this invention by reacting it with a boron compound capable of introducing boron into the molecule. Boron compounds useful for this purpose include boron acids, (e.g. $H_3BO_3$, $H_2B_4O_7$, $HBO_2$ and the like), salts or boron acids with weak base (e.g., ammonium borate, lower alkyl ammonium borates, and the like), esters of boron acids, (e.g., trimethyl borate, triethyl borate, tri-n-propyl borate, tri-isobutyl borate, and the like), boron oxides, boron halides (e.g., $BF_3$, $BCl_3$), boron salts of oxy acids (e.g. boron phosphate, boron nitrate, boron acetate, boron propionate, boron butyrate, and the like). Mixtures of the above boron compounds can also be used.

The use of complexes of a boron trihalide with ethers, organic acids, inorganic acids, or hydrocarbons is a convenient means of introducing the boron reactant into the reaction mixture. Such complexes are known and are exemplified by boron trifluoride-diethyl ether, boron trifluoridephosphoric acid, boron trichloride-chloroacetic acid, boron tribromide-di-oxane, and boron trifluoride-methyl ethyl ether.

Specific examples of boronic acids include methyl boronic acid, phenyl-boronic acid, cyclohexyl boronic acid, p-heptylphenyl boronic acid and dodecyl boronic acid.

The boron acid esters include especially mono-, di-, and tri-organic esters of boric acid with alcohols such as e.g., methanol, ethanol, isopropanol, cyclohexanol, cyclopentanol, 1-octanol, 2-octanol, dodecanol, behenyl alcohol, oleyl alcohol, stearyl alcohol, benzyl alcohol, 2-butyl cyclohexanol, ethylene glycol, propylene glycol, trimethylene glycol, 1,3-butanediol, 2,4-hexanediol, 1,2-cyclohexanediol, 1,3-octanediol, glycerol, pentaerythritol, diethylene glycol, Carbitol, Cellosolve, triethylene glycol, tripropylene glycol ethylenechlorohydrin, 6-bromo-octanol, and 7-keto-decanol. Lower alcohols, 1,2-glycols, and 1-3-glycols, i.e., those having less than about 8 carbon atoms are especially useful for preparing the boric acid esters for the purpose of this invention.

Methods for preparing the esters of boron acid are known and disclosed in the art (such as "Chemical Reviews", pages 959–1064, volume 56). Thus, one method involves the reaction of boron trichloride with 3 moles of an alcohol or a phenol to result in a tri-organic borate. Another method involves the reaction of boric oxide with an alcohol or a phenol. Another method involves the direct esterification of tetraboric acid with 3 moles of an alcohol or a phenol. Still another method involves the direct esterification of boric acid with a glycol to form, e.g. a cyclic alkylene borate.

The boronation can be carried out by merely mixing the boronating agent with the amide intermediate and heating the mixture to reaction temperature. The temperature should be high enough to cause a reaction to introduce boron into the amide intermediate but not so high as to cause extensive decomposition of the amide intermediate or boronated product. A useful range is about 50°–300° C. A preferred range is about 75°–200° C. Under these conditions the boronation is usually complete in about 0.5–8 hours.

The amount of boronating agent used should be an amount sufficient to supply at least 0.01 atoms of boron per nitrogen atom in the boronated product. An amount in excess of this is generally used in the boronation. Preferably, the amount of boronating agent mixed with the amide intermediate should be enough to supply 0.01 to about 0.5 boron atoms per nitrogen atom. In practice, larger amounts are generally used and any excess removed after the boronation by standard means such as filtration or washing with water, alcohols or mixtures thereof.

Although a solvent is not required, it is sometimes helpful due to the viscous nature of the amide intermediate to use a solvent. Useful solvents include hydrocarbons such as hexane, octane, nonane, toluene, xylene, mineral oil, and the like. Also, chlorinated hydrocarbons such as chlorobenzene, dichlorobenzene, and the like, can be used.

The following examples illustrate the manner by which the initial alkylphenoxy-substituted aliphatic carboxylic acid and esters can be prepared.

EXAMPLE 1

Preparation of PIB Phenoxy Acetic Acid (a) Preparation of sodium PIB phenate.

A p-PIB substituted phenol (equivalent weight 1130) was prepared by alkylation of phenol, in the presence of a boron trifluoride/phenol complex, with a PIB of molecular weight 1000. To a solution of the resulting PIB phenol (79 g., 0.07 m.) in petroleum ether (30 ml., b.pt. = 100/120° C.) was added a solution of sodium methoxide in methanol, prepared from sodium metal (1.61 g., 0.07 m.) and anhydrous methanol (25 ml). After stirring for 30 mins., the product vacuum stripped to 150° C.

(b) Reaction of sodium PIB phenate with chloroacetic acid.

To a solution of the sodium PIB phenate prepared in (a) (75g. 0.065 m.) in petroleum ether (50 ml., b.pt. = 100/120° C.) was added chloroacetic acid (7 g., 0.074 m.) and a solution of sodium methoxide in methanol, prepared from sodium metal (1.7 g., 0.074 m.) and anhydrous methanol (20 ml.). The mixture was heated, with stirring, under nitrogen, at 100° C. for 3 hours. After allowing to cool the product was further diluted with petroleum ether, washed with 200 ml. of dilute hydrochloric acid, followed by three 200 ml. portions of water, dried over anhydrous magnesium sulphate, vacuum stripped to 170° C. and finally filtered.

Acidity = 19 mg. KOH/g.

EXAMPLE 2

Preparation of n-Butyl polyisobutylphenoxyacetate

To a solution of PIB phenol (107.0 g., 0.1 m.), prepared by alkylation of phenol with 1000 molecular weight polyisobutylene using a BF$_3$/ phenol complex as catalyst, and n-butyl chloroacetate (22.6 g., 0.15 m.) in xylene (100 ml.) was slowly added, over about one hour, a solution of sodium methoxide (8.1 g., 0.15 m.) in anhydrous methanol (40 ml.). The addition was carried out at 100° C. and on completion the solution was heated at this temperature for a further one hour. The solution was washed with 10% hydrochloric acid (50 ml.) followed by a 3 × 80 ml. portions of aqueous methanol (1:4). After being dried over magnesium sulphate the solution was stripped of solvent.

Yield = 102 g.

A sample of this product was saponified with excess aqueous potassium hydroxide, acidified with hydrochloric acid and then washed with portions of aqueous methanol (1:4) until acid free. The acid value of the thus formed PIB phenoxy acetic acid (36.5 mg. KOH/g.) indicated that a conversion of 73% had been obtained.

The following example illustrates the conversion of the initial alkylphenoxy aliphatic carboxylic acid ester to the amide intermediate.

EXAMPLE 3

A mixture of 50 g. of polyisobutylphenoxy butyl acetate from Example 2 and 3 g. of tetraethylenepentamine was heated to 200° C. and stirred at that temperature for 4 hours. Butanol which formed during the amidation was allowed to distil out. After dilution with mineral oil the mixture was filtered to obtain a clear product analyzing: N — 1.8%, acidity — 5 mg KOH/g, total base No. (TBN) 37 mg KOH/g.

EXAMPLE 4

In a reaction vessel was placed 25.84 Kg of n-butyl polyisobutyl (m.w. 1000) phenoxy acetate. Over a one hour period, 1.64 Kg of tetraethylene pentamine was added while heating to 200° C. The mixture was stirred for 4 hours at 200° C. at 50 mm. while distilling out n-butanol. The product was diluted by adding neutral mineral oil to form a concentrate containing 15 wt.% oil. Its analysis was %N — 1.75; TBN 39.

EXAMPLE 5

In a reaction vessel was placed 24.75 Kg of n-butyl polyisobutyl (m.w. 1000) phenoxy acetate. Under a nitrogen atmosphere this was heated to 170° C. and 1.68 Kg of tetraethylenepentamine added over a 45 minute period while maintaining vacuum at 140 mm. Temperature was then raised to 200° C. over a 50 minute period and the mixture stirred at 200° C. for 4 hours. It was then diluted with mineral oil as in Example 4, and analyzed 2.03% nitrogen.

The following examples illustrate the boronation of the amide intermediate.

EXAMPLE 6

In a reaction vessel was placed 800 g. of the polyisobutylphenoxy acetamide of tetraethylenepentamine from Example 4. To the reaction vessel was added 61.8 g. of boric acid ($H_3BO_3$). This mixture was stirred at 160° C. for 4 hours while passing a slow stream of nitrogen through the vessel to aid in water removal. Following this the product was filtered while at 100° C. The product analyzed: N — 1.7%, B — 0.32%, TBN 28.9, giving a B:N atom ratio of 0.24:1.

EXAMPLE 7

The procedure of Example 6 was repeated using 15.5 g. of boric acid. The product analyzed: N — 1.72%, B — 0.29%, TBN 34.9, giving a B:N atom ratio of 0.22:1.

EXAMPLE 8

The procedure of Example 6 was repeated using 1000 g. of the polyisobutylphenoxy acetamide of tetraethylenepentamine and 19.3 g. of boric acid. The mixture was stirred for 3 hours at 160° C. and filtered to remove unreacted boric acid. The product analyzed: N — 1.73%, B — 0.32%, TBN 36.4, giving a B:N atom ratio of 0.24:1.

From the above, it is apparent how the procedure can be carried out with any of the amides of alkylphenoxysubstituted aliphatic carboxylic acids as previously described. These other amide intermediates are merely substituted for the polyisobutylphenoxy acetamide of tetraethylenepentamine in Examples 6-8.

Likewise, any of the wide variety of boron compounds previously described can be substituted for boric acid in Examples 6-8 to give similar boronated products.

The boronated products of this invention are used as dispersants in lubricating oil. They are especially useful in lubricating oils used in internal combustion engines. Concentrations of about 0.25-5 weight percent in the oil give excellent results.

When used in lubricating oils the oils are usually blended with other additives conventionally used in such oils such as zinc dialkyldithiophosphates, calcium alkaryl sulphonates, overbased calcium alkaryl sulphonates, barium phenates, thio-bridged barium or calcium phenates, phosphosulphurized polyolefins such as phosphosulphurized polyisobutylene, benzotriazoles, V.I. improvers such as poly alkylmethacrylates, polyisobutylene, ethylene-propylene copolymers, styrene-butadiene copolymers, phenolic antioxidants such as 4,4'-methylenebis(2,6-di-tert-butylphenol), α-dimethylamino2,6-di-tert-butyl-p-cresol, and the like.

Tests were carried out which demonstrate the superior properties of the boronated dispersants of this invention compared to the unboronated material. These tests were the MS IIc and IIIc, L-38 and Petter AV-B engine tests. In the first three of these tests the oil used was a fully formulated SAE 10W/30 mineral oil containing conventional commercial additives including a metal sulphonate, zinc dialkyldithiophosphate, a V.I. improver, and the like, in which the dispersant normally used was replaced with either an alkylphenoxy acetamide of tetraethylenepentamine or its boronated counterpart.

The IIc and IIIc tests are standard engine tests described in ASTM Special Technical Publication 315-F. The IIc test is designed to evaluate the rusting and corrosion characteristics of motor oils. A standard test engine is operated continuously for 28 hours at moderate engine speed, partially warmed-up coolant and rich air/fuel ratio. The engine is then operated 2 hours at elevated coolant temperature and then shut down for 30 minutes. This is followed by 2 hours further operation at higher temperature and lean air/fuel ratio.. Following this, the engine is disassembled and various parts visually inspected to determine the extent of rust and corrosion. The parts are rated on a scale of from 0–10, with 10 being clean. The overall rating is an average of the rating of the various parts.

The following Table 1 compares the IIc results obtained with a polyisobutylphenoxy acetamide of tetraethylenepentamine with the results obtained with the same type of product after boronation. Both dispersants were used at 3% concentration in a formulated motor oil in which they replaced the dispersant normally used.

TABLE 1

| Additive | Rust Rating |
|---|---|
| unboronated alkylphenoxyacetamide | 5.9, 6.8, 7.1 (avg. 6.6) |
| boronated alkylphenoxyacetamide | 6.9 |

The above results show that the boronation has somewhat improved the rust and corrosion protection provided by the oil.

The IIIc test evaluates the high temperature oil thickening characteristics, sludge and varnish deposits as well as engine wear. A standard test engine is operated under non-cyclic, moderately high speed, high load and temperature conditions for 64 hours. Oil samples are withdrawn at 8 hour intervals and viscosity measurements made. Following the test the pistons are examined for ring land face varnish and rated on a scale from 0–10, with 10 being clean. The test additives were used at 1.8% concentration in a formulated motor oil in which they replaced about one-half of a commercial succinimide dispersant normally used in this oil. The results of the test are shown in the following Table 2.

TABLE 2

| Additive | Viscosity Increase | | |
|---|---|---|---|
| | 40 hrs. | 64 hrs. | Varnish |
| unboronated alkylphenoxyacetamide | 41% | 1452% | 4.7 |
| boronated alkylphenoxyacetamide | 24% | 189% | 7.95 |

These tests show a sharp increase in the stability of the oil containing the boronated alkylphenoxyacetamide as evidenced by a much lower increase in oil viscosity during the test. The test also showed a very significant improvement in the piston ring land face varnish due to the boronation.

The L-38 test is a standard engine test described in the Coordinating Research Council (CRC) Report No. 426 (1969). The test is designed to study the copper-lead corrosion characteristics of motor oils during engine operation. The test involves the continuous operation of a single cylinder CLR test engine under constant speed conditions for 40 hours. The bearing weight loss during the test is determined in mg and is a measure of the corrosivity of the oil. Results obtained in this test using 3% test additive in a formulated oil in which the test additive replaced the dispersant normally used were as follows:

TABLE 3

| Additive | Bearing Wt. Loss (mg) |
|---|---|
| unboronated alkylphenoxyacetamide | 51, 71 |
| boronated alkylphenoxyacetamide | 24.5 |

As the above results show, the boron-treated alkylphenoxyacetamide gave less than one-half the amount of bearing weight loss compared to the same type additive without boronation.

The Petter AV-B test is a standard engine test described by the Coordinating European Council (CEC) in Bulletin CECL-13-T-74. The test measures the ability of the oil to prevent excessive piston ring groove deposits and to prevent the formation of excessive deposits on the piston of supercharged diesel engines under continuous operation at high temperature. It utilizes a Petter AV-B laboratory test engine. The engine is operated at high speed and at a moderately high ring belt temperature for 50 hours. It is then disassembled and the piston grooves, lands, skirt and undercrown rated on a scale from 0–10, with 10 being clean. These ratings are averaged and factored to a scale of 0–100, with 100 being clean, to give an overall rating. The test method employed was the Institute of Petroleum standard method 279/72T.

Comparative results obtained using an SAE 30 monograde oil formulated for diesel use containing 1.5% of the test additive were as follows:

TABLE 4

| Additive | Overall Rating |
|---|---|
| unboronated alkylphenoxyacetamide | 60.0, 59.4 |
| boronated alkylphenoxyacetamide | 66.4 |

These results show that even under severe diesel operating conditions the boronated alkylphenoxyacetamide outperforms the corresponding unboronated additive.

The novel additives of this invention are useful in preparing additive concentrates for addition to lubricating oil to provide a balance of properties to meet recognized industry standards. These concentrates contain about 15–50% diluent oil, about 5–75% boronated amide of an alkaryloxy-substituted alkanoic acid as previously described, and the balance other conventional lubricating oil additives such as zinc dialkyldithiophosphates, zinc dialkaryldithiophosphates, neutral and overbased calcium and magnesium sulphonates, neutral and overbased calcium or barium phenates, thiobridged calcium or barium phenates, phosphosulphurized polyolefins, e.g., phosphosulphurized polyisobutylene (m.w. 1000), barium salts of phosphosulphurized polyolefins, sulphurized isobutylene, phosphosulphurized terpenes, V.I. improvers such as polyalkylmethacrylates, e.g., polylaurylmethacrylate, polyisobutylene, ethylenepropylene copolymer, styrene-butadiene copolymer, metal deactivators, e.g., benzotriazoles, phenolic antioxidants, e.g., 4,4'-methylenebis(2,6-di-tert-butylphenol) α-dimethylamino-2,6-di-tert-butyl-p-cresol, and other conventional additives.

It is expected that the additives of this invention are also useful on addition to fuels such as diesel fuel and gasoline. In such use they would maintain cleanliness in the fuel induction system.

We claim:

1. A boronated product useful as a lubricating oil dispersant made by reacting an initial compound having the formula:

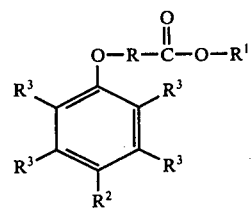

wherein:
(a) each $R^3$ is the same or different and is a hydrogen atom, an alkyl group containing from 1 to about 16 carbon atoms, a halogen atom, or one $R^3$ group in the ortho position relative to the oxygen atom is a group of the formula:

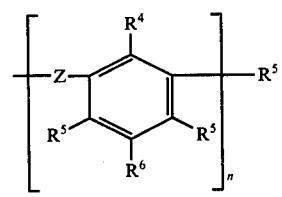

in which
(i) n is an integer from 1 to 6,
(ii) each Z is the same or different and is a methylene group or a sulfur chain of formula $-(S)_m-$ wherein m is from 1 to 4,
(iii) each $R^4$ is the same or different and is a hydrogen atom, an alkyl group containing from 1 to 16 carbon atoms, a halogen atom, a hydroxyl group or a group of formula

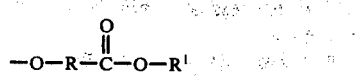

(iv) each $R^5$ is the same or different and is a hydrogen atom, an alkyl group containing from 1 to 16 carbon atoms, a halogen atom, or a hydroxyl group, provided that one of, but not more than one of, $R^4$ and $R^5$ is a hydroxyl group, (v) each $R^6$ is the same or different and is a hydrogen atom, an alkyl group containing 1 to 29 carbon atoms, a halogen atom or is as $R^2$, provided that one group $R^3$ in the ortho position relative to the oxygen atom attached to the aromatic nucleus is a hydrogen, a halogen, or a methyl or ethyl group, (b) each R is the same or different and is a straight or branched chain alkylene group containing from 1 to 20 carbon atoms, (c) each $R^1$ is the same or different and is a hydrogen atom or the ester residue of an alkanol containing from 1 to 5 carbon atoms, and (d) each $R^2$ is the same or different and is an alkyl group containing at least 30 carbon atoms;

with about 0.5 to 10 equivalents per mole of said initial compound of an amine containing a reactive hydrogen atom bonded to nitrogen to form an amide and reacting said amide with a boron compound capable of introducing boron into the molecule, said boron compound being selected from the group consisting of boron acids, salts of boron acids, esters of boron acids, boron oxides, boron halides and boron salts of oxygen acids, to obtain a boronated product containing at least 0.01 atoms of boron per nitrogen atom.

2. A boronated product of claim 1 wherein $R^3$ is a hydrogen atom.

3. A boronated product of claim 2 wherein R is a methylene group.

4. A boronated product of claim 3 wherein $R^2$ is a polyolefin group containing 50–200 carbon atoms.

5. A boronated product of claim 4 wherein $R^1$ is the ester residue of an alkanol containing 1 to 5 carbon atoms.

6. A boronated product of claim 4 wherein said amine is an alkylene polyamine.

7. A boronated product of claim 5 wherein said amine is an alkylene polyamine.

8. A boronated product of claim 6 wherein said boron compound is a boron acid.

9. A boronated product of claim 7 wherein said boron compound is a boron acid.

10. A boronated product of claim 9 wherein said boron acid is a boric acid.

11. A process for making a boronated lubricating oil additive, said process comprising reacting an initial compound having the formula:

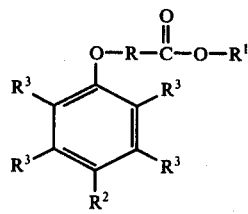

wherein:

(a) each $R^3$ is the same or different and is a hydrogen atom, an alkyl group containing from 1 to about 16 carbon atoms, a halogen atom, or one $R^3$ group in the ortho position relative to the oxygen atom is a group of the formula:

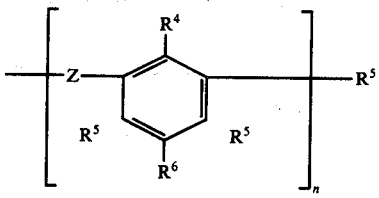

in which
(i) n is an integer from 1 to 6,
(ii) each Z is the same or different and is a methylene group or a sulfur chain of formula $-(S)_m$ wherein m is from 1 to 4,
(iii) each $R^4$ is the same or different and is a hydrogen atom, an alkyl group containing from 1 to 16 carbon atoms, a halogen atom, a hydroxyl group or a group of formula

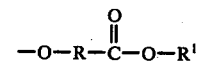

(iv) each $R^5$ is the same or different and is a hydrogen atom, an alkyl group containing from 1 to 16 carbon atoms, a halogen atom, or a hydroxyl group, provided that one of, but not more than one of, $R^4$ and $R^5$ is a hydroxyl group, (v) each $R^6$ is the same or different and is a hydrogen atom, an alkyl group containing 1 to 29 carbon atoms, a halogen atom or is as $R^2$, provided that one group $R^3$ in the ortho position relative to the oxygen atom attached to the aromatic nucleus is a hydrogen, a halogen, or a methyl or ethyl group, (b) each R is the same or different and is a straight or branched chain alkylene group containing from 1 to 20 carbon atoms, (c) each $R^1$ is the same or different and is a hydrogen atom or the ester residue of an alkanol containing from 1 to 5 carbon atoms, and (d) each $R^2$ is the same or different and is an alkyl group containing at least 30 carbon atoms;

with about 0.5 to 10 equivalents per mole of said initial compound of an amine containing a reactive hydrogen atom bonded to nitrogen to form an amide and reacting said amide with a boron compound capable of introducing boron into the molecule, said boron compound being selected from the group consisting of boron acids, salts of boron acids, esters of boron acids, boron oxides, boron halides and boron salts of oxygen acids, to obtain a boronated product containing at least 0.01 atoms of boron per nitrogen atom.

12. A process of claim 11 wherein $R^3$ is a hydrogen atom.

13. A process of claim 12 wherein R is a methylene group.

14. A process of claim 13 wherein $R^2$ is a polyolefin group containing 50–200 carbon atoms.

15. A process of claim 14 wherein $R^1$ is the ester residue of an alkanol containing 1 to 5 carbon atoms.

16. A process of claim 14 wherein said amine is an alkylene polyamine.

17. A process of claim 15 wherein said amine is an alkylene polyamine.

18. A process of claim 16 wherein said boron compound is a boron acid.

19. A process of claim 17 wherein said boron compound is a boron acid.

20. A process of claim 19 wherein said boron acid is boric acid.

21. A lubricating oil composition comprising a major amount of lubricating oil containing a dispersant amount of a boronated product of claim 1.

22. An additive concentrate which when added to lubricating oils will impart a balance of desirable properties to said lube oil, said concentration comprising about 15–50% diluent oil and about 5–75% boronated product of claim 1.

* * * * *